United States Patent
Cliche et al.

(10) Patent No.: US 6,953,487 B2
(45) Date of Patent: Oct. 11, 2005

(54) METALLIC GAS CELLS AND METHOD FOR MANUFACTURING THE SAME

(75) Inventors: Jean-François Cliche, Charlesbourg (CA); Michel Têtu, Cap-Rouge (CA); Nicolas Côte, St-Augustin (CA); Sébastien Tranchart, Québec (CA)

(73) Assignee: Teraxion Inc., Sainte-Foy ( * ) Notice: Subject to any disclaimer, the term of this patent is extended or adjusted under 35 U.S.C. 154(b) by 293 days.

(21) Appl. No.: 10/391,482

(22) Filed: Mar. 18, 2003

(65) Prior Publication Data

US 2004/0004720 A1 Jan. 8, 2004

Related U.S. Application Data

(60) Provisional application No. 60/365,159, filed on Mar. 19, 2002.

(51) Int. Cl.$^7$ .............................. H01S 4/00; H01M 6/42; G01N 21/00
(52) U.S. Cl. ..................... 29/623.2; 29/592.1; 356/246; 136/255; 429/101
(58) Field of Search ................................. 356/244, 246, 356/326, 440; 29/623.2, 592.1, 185; 136/255, 251; 429/149, 101; 250/343, 373

(56) References Cited

U.S. PATENT DOCUMENTS

| | | | | |
|---|---|---|---|---|
| 3,589,945 A | * | 6/1971 | Christopher et al. .......... 429/27 |
| 4,119,363 A | | 10/1978 | Camlibel et al. .......... 350/96.2 |
| 4,676,639 A | * | 6/1987 | Van Wagenen ............. 356/246 |
| 4,889,406 A | | 12/1989 | Sezerman ................. 350/96.21 |
| 5,025,448 A | | 6/1991 | Sudo et al. .................... 372/32 |
| 5,116,759 A | | 5/1992 | Klainer et al. |
| 5,204,270 A | * | 4/1993 | LaCount ..................... 436/157 |
| 5,268,922 A | | 12/1993 | Fouere et al. ................. 372/98 |
| 5,327,105 A | | 7/1994 | Liberman et al. .......... 331/94.1 |
| 5,418,087 A | * | 5/1995 | Klein .......................... 429/101 |
| 5,500,768 A | | 3/1996 | Doggett et al. ............. 359/652 |
| 5,780,843 A | | 7/1998 | Cliche et al. ................ 250/226 |
| 5,793,916 A | | 8/1998 | Dahringer et al. ............ 385/95 |
| 5,897,927 A | | 4/1999 | Tsai et al. |
| 6,117,195 A | * | 9/2000 | Honegger ................... 29/632.2 |
| 6,142,678 A | | 11/2000 | Cheng .......................... 385/79 |
| 6,215,366 B1 | | 4/2001 | Kern et al. ................. 331/94.1 |
| 6,275,288 B1 | * | 8/2001 | Atkinson et al. ........... 356/246 |
| 6,421,120 B1 | | 7/2002 | Wildnauer ................ 356/243.1 |
| 6,439,040 B1 | | 8/2002 | Garms et al. |
| 2002/0118463 A1 | | 8/2002 | Wu et al. .................... 359/639 |

FOREIGN PATENT DOCUMENTS

DE      19831457 A1      7/1999

* cited by examiner

Primary Examiner—Gregory J. Toatley, Jr.
Assistant Examiner—Sang H. Nguyen
(74) Attorney, Agent, or Firm—Fogg and Associates, LLC; Laura A. Ryan

(57) ABSTRACT

A metallic gas cell including a metallic casing having an input open end and an output open end, and a opening located therebetween. The metallic gas cell also includes an input and an output optical modules, each being respectively hermetically attached to one of the corresponding open ends. The metallic gas cell includes sealing means for sealing each of the optical modules in one of the corresponding open ends, thereby defining an airtight cavity in the casing when the opening is sealed. The metallic gas cell also includes an optical energy absorbing gas being enclosed within the cavity. The metallic gas cell is advantageously modular for allowing the use of various input or output modules such as windows, lenses, lasers, photodetectors, and fiber collimators. The gas cell also allow multi-cavity gas cell that that use a minimum number of components and cells to be obtained. Moreover, by its specific construction, the present gas cell prevents alignment issues. There is also provided a method for manufacturing such a metallic gas cell.

6 Claims, 9 Drawing Sheets

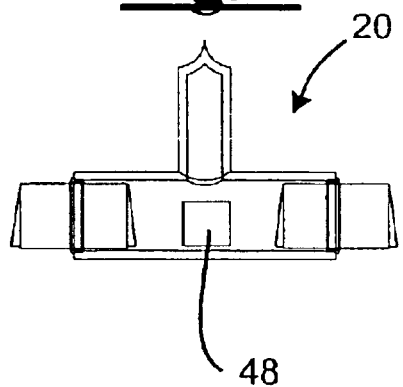
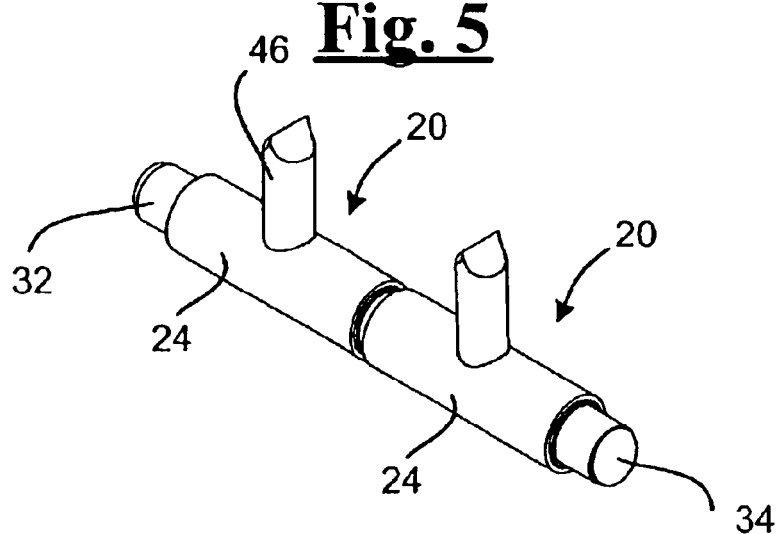
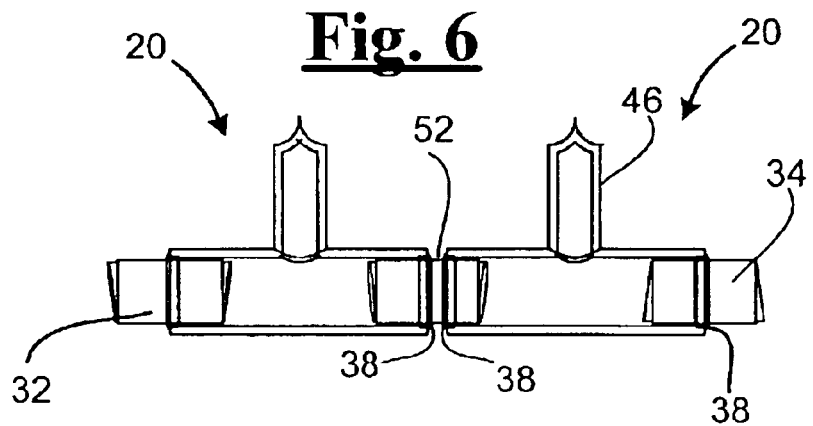

METALLIC GAS CELLS AND METHOD FOR MANUFACTURING THE SAME

CROSS REFERENCE TO RELATED APPLICATIONS

This application is related to and claims the benefit of the filing date of co-pending provisional application Ser. No. 60/365,159 (the "'159 Application"), filed on Mar. 19, 2002. The '159 Application is incorporated by reference

FIELD OF THE INVENTION

The present invention generally relates to optical devices and more particularly concerns a metallic gas cell and a method for manufacturing such a metallic gas cell.

BACKGROUND OF THE INVENTION

Gas references are widely used in numerous applications involving optical signals. Indeed, light can interact in various fashions with gases, depending on the type of light signal, the type of gases and the optical configuration used.

One application of gas cells for using with optical signals is the absolute referencing of the optical frequency of a light signal from a device such as a laser. Indeed, if the gas has a well known light absorption characteristics with optical frequency, the gas can be used as an absolute reference filter to accurately determine the light frequency and eventually control it.

There are a number of applications that use laser sources and wherein absolute, calibration-free knowledge of the frequency of the laser is very desirable for better performance and long life. For instance, wavelength division multiplexed (WDM) communication system offer a high data transmission capacity by allowing multiple laser sources to transmit many high-speed data channels simultaneously into a single fiber, where each channel is transmitted at a unique optical frequency (or wavelength). In order to standardize the frequencies of the channels across telecommunication systems, the industry has adopted a standard which specify that the nominal optical frequency of every channel should be at an integer multiple of 100 GHz, 50 GHz, 25 GHz or even smaller spacings with a typical accuracy within 2.5 GHz, 1.25 GHz or even better as the grid density increases. Semiconductor lasers currently used in telecommunication systems do not intrinsically generate frequencies accurate or stable enough to be used in such dense frequency grids because current fabrication technologies do not permit to know with sufficient accuracy the nominal frequency of the lasers, and the frequency of the laser varies significantly with operating conditions and environmental factors such as temperature and ageing. For these reasons there is a need to stabilize the frequency of semiconductors to a predetermined value with a sufficient accuracy by using an optical reference element to compare the frequency of the laser with the predetermined value and generate an error signal which is fed back to the laser to correct its frequency. Different optical references have been used on the past to stabilize semiconductor lasers. Some atomic or molecular gases, for instance, exhibit absorption lines in the optical frequency range of telecommunication networks. The frequency of these absorption lines is determined by quantum mechanical laws and is generally extremely precise and stable with respect to environmental factors. Furthermore, the width of the absorption lines is very narrow, which allows for very sensitive frequency drift detection. Once properly frequency-locked to an absorption line, a laser can display frequency accuracy and stability orders of magnitude better than is required for current telecommunications systems. Gas cells are therefore a reference of choice for those high frequency accuracy applications.

Another application where gas cells are used in combination with an interrogating optical beam is spectroscopy. Gas analysis systems typically use a gas cells to hold a gas sample whose composition is to be determined. A broadband light source is used to generate a light beam that is passed through the gas in the cell, and a spectrometer measure the resulting light spectrum. The dips in the measured spectrum shows at which frequencies the gas has absorbed the light and with which intensity. The composition of the gas can then be deduced by processing the absorption spectrum. Such application may be used, for example, for sensing of foreign substances.

Other type of spectrometers or gas analysis devices may use narrowband light sources to interrogate a gas and determine the concentration of specific substances. These may use narrowband sources such as a tunable or fixed-frequency lasers. These instruments work by passing the laser light through the gas inside an optically transparent gas cell and by measuring its absorption at one or many frequencies. The composition of the gas can then be deduced by processing the absorption values. Such a system can be as simple as a laser probing one optical frequency only which is known to be absorbed when a gas is present. Such a calibration technique us described in U.S. Pat. No. 5,780,843.

Spectrometers such as the ones described before may require calibration to ensure the measured frequencies and absorption level are accurate. To achieve high accuracy, samples of known gases are stored in sealed cells as references for spectroscopic quantities, and are optically interrogated by the spectrometer to measure their spectrum and recalibrate the spectrometer amplitude and frequency scale.

Optical measurements instruments such as Optical Spectrum Analyzers (OSA), performance monitoring systems and other spectrum analysis devices can also advantageously use gas cells as calibration devices. Many commercial OSA now possess an internal gas cell containing a well-known gas. The light from a broadband source such as a LED is passed through the cell and its spectrum is recorded by the instrument. The measured spectrum is then analyzed to find frequency calibration points from known absorption lines of the gas and can therefore compensate frequency offsets and drifts of the instruments. Acetylene gas cells are commonly used as references at wavelength around 1530 nm. The use of a gas cell to calibrate an OSA is described in U.S. Pat. No. 6,421,120.

Heterodyne-based optical spectrum analyzers are another kind of spectral analysis devices. These use the heterodyning between a local tunable laser source and the user optical signal to measure the power spectrum the user signal with a very high resolution. An internal gas cell can also be used to frequency-calibrate the local tunable laser by measuring and analyzing the known absorption lines observed when the laser is tuned.

Different types of gas cells exist on the market. Gas cells made entirely of glass are very common. Since they are made entirely of glass, the two ends of the cells are made of transparent materials and allow for a light beam to pass through them an be absorbed by the gas inside. Glass cell present several drawbacks, however. First, conventional glass cells are not very compliant to mechanical stresses and are fragile. Consequently, they are less useful in aerospace applications or in industrial environment or portable equipment where shocks and prolonged vibrations can jeopardize the cell structure and its hermeticity. Second, glass gas cells involve high temperatures for sealing. Indeed, such cells typically possess a glass filling tube attached to the side of the cell. Typical assembly techniques consist in connecting a vacuum pump to the filling tube, by emptying the cell, and by introducing the desired gas. Then a portion of the filling tube is heated until the glass softens and part of the tube collapses upon itself under the internal vacuum pull. This, effectively seals the cell. The high temperatures required to soften the glass may cause the gas inside the cell to react and loose its chemical properties. Special type of glasses may be used to allow a lower melting point, but the required temperatures are still relatively high. Furthermore, the sealing process described above is often done manually by people skilled in fused glass manipulation. This sealing process is however more difficult or expensive to implement in fabrication chains with reliable seal quality, and the geometry of the sealed filling tube is hard to control accurately. High quality glass cells are therefore expensive to fabricate.

In order to avoid using high temperatures for sealing the glass gas cell, organic sealants such as glue or epoxy could be used to seal the glass filling tube. Such materials, however, are subject to degradation with time and may be affected by exposure to moisture or other chemicals. Organic sealants generally let gases slowly diffuse through them and are not considered hermetic. Telecommunication components which are subject to the harsh Telcordia reliability requirements generally keep all organic glues within a moisture-free hermetic package which is sealed by soldering, brazing or welding in order to prevent degradation.

Another disadvantage of glass cell is that glass is not a convenient material to shape or modify. It is harder to shape the glass cell into the desired format, especially if the interior of the cell is kept at very low pressures compared to atmospheric pressures.

Thus, in order to avoid the limitations of glass cells, many applications rely on using metallic gas cells to contain a gas that can be interrogated by a light beam. Such cells are potentially more robust and flexible than glass cells. However, these cells must still possess optical windows to allow the light to pass through the gas.

There is in the art a few kind of metallic cells that can be used with optical signals. Examples of those can be found in applications such as optically-pumped rubidium or cesium clocks. In these applications, a light beam is sent inside the metallic cavity to excite a gas, which then resonates at microwave frequencies. The metal cavity also serves as a microwave resonator and allow the atoms to continue resonating at their natural frequency which is very stable and precise. Some of the microwave signal is extracted from the cavity to serve as a accurate frequency standard from which precise time measurement systems can be built. U.S. Pat. No. 5,327,105 describe such a gas cell used for a miniaturized atomic frequency standard.

Industrial system also use metal enclosures to contain a gas while allowing to probe it with a light source. These systems are often made of stainless steel tubes bolted together in various configurations with flange joints and hermeticity rings made of rubber or soft metals. Optical windows made of glass or other transparent materials are secured and sealed onto the main assembly through additional flanges and bolts. To use the system, gases from an industrial process are made to flow inside the metal tubing, and light is passed through the gas through the windows. A spectrometer or other instrument can then be used to analyze that light and determine the process gas composition.

Optical modules used in telecommunications are other examples of metallic enclosures which allow light in or out and are hermetic. A typical laser module, for example, consists in a square Butterfly-type package in which all the optical components, including the laser source, are glued or otherwise attached. A metallized optical fiber passes through an opening on one wall and is hermetically soldered to that wall. Once the components are in place, a lid is placed on the package and is hermetically soldered by welding, soldering or brazing, generally in an inert moisture-free gas such as nitrogen. This results in a metallic cavity filled with nitrogen with an optical output port (the fiber). Another example of sealed optical component are photodetectors, which may be packaged in a can-type package with an hermetic window. The photodetector chip is placed in the can, generally filled with an inert, moisture-free gas. Its surface can receive optical energy through the window placed at the other end of the can.

Optical components such as the ones described above are not designed to withstand very low vacuum levels, and generally make no provision for connecting a vacuum system as there is no filling tube or hole.

Some specialized opto-electronic components, such as photomultiplicator tubes or bolometers, are vacuum-tight components that have windows to allow light to enter the inside of an evacuated cavity. These devices are not designed to allow a light beam to interrogate a gas in order to use it as a optical reference.

One main disadvantage of the metallic gas cells described above is that these components are often manufactured from many components, v.i.z. side walls, windows, floor, sealed lid, etc. All these components need to be attached together hermetically, and a number of joints have to be sealed perfectly to maintain a good vacuum for long periods. In such set-ups, the total number of hermetic joints is not minimized, a situation which increases the risk of leaks and device failure. Having to assemble these components also make the device expensive to fabricate.

One improved method of fabrication for these metallic gas cells would be to use molded or pressed metal enclosures on which lids are hermetically attached. Although this would minimize the number of hermetic seals, the total length of the seals would still not be minimized.

Another disadvantage of previously described metallic gas cells is that the structure of these cells do not allow easy alignment of the input or output optical components. In many applications where gas cells are required, the light beam that enter the cell must keep a very accurate alignment to reach the other end of the cell at a very precise point and with a very accurate angle. The previously metallic gas cells do not have mechanical structure that allows to point a beam accurately enough to adequately hit a small surface detector, a fiber collimator, or any other target at the exterior of the cell.

As has been shown above, metallic gas cells do bring a number of advantages compared to glass cells, although a number of structural properties would need to be improved in order to provide cheap, reliable and very accurate gas cells. There are also a number of additional features that are lacking in gas cell currently available. Those are discussed thereafter.

There are applications where it is not sufficient to have only one gas reference and where multiple gas references may be needed, for example to be interrogated by a laser, spectrometer or OSA. For example, a widely tunable laser may use the absorption lines of a gas to calibrate its frequency tuning characteristics, but a single gas may not provide absorption lines over the whole frequency tuning range of the laser, which does not allow the laser to be fully calibrated over its full range. In some cases, it may be possible to mix within a single gas cell multiple gases having various absorption lines at various frequencies to provide the requires calibration points over the full tuning range of the laser or the instrument. However, some gases cannot be mixed because they react with one another, or the presence of other gases broadens or shifts the absorption lines, therefore reducing their accuracy. In such situations, multiple independent gas cells must be used, but each cell require their own hermetic input and output port (window, fiber collimator etc.). This increases the number of interfaces the light beam must cross while going through the cells. This brings the disadvantages of increased part count, increased cost, and increased optical losses. Current gas cells designs do not allow to efficiently cascade multiple gas cells while minimizing these drawbacks.

Another commonly found drawback with current gas cells is that they require an additional, independent fiber collimator in order to use them with an fibered input or output signal. Indeed, many applications use optical fiber to bring light into a gas cell. The light exiting the fiber has to be collimated in order to pass through the gas, therefore requiring a fiber collimator. This collimator, which consists in a fiber attached to a lens, is installed in front of the input window of the gas cell. This bring a number of disadvantages. First, the light exiting the fiber has to go through two optical components, that is, the lens and the cell window, before reaching the gas. This increases the number of optical components, the optical losses and the risk of parasitic optical resonances. Second, since the fiber collimator is mechanically independent from the gas cell, the alignment of the collimated beam into the cell may inadvertently change with external mechanical stresses. None of the existing cells integrate a collimator into the cell itself for eliminating components and providing a better performance and alignment stability. The same limitations exists if there is a need to collimate the beam exiting from the cell into a fiber.

Similar limitations have been found in applications which require the beam exiting a conventional gas cell to be sent onto a packaged photodetector. In these applications, the light beam must exit the gas through the cell window, will cross the photodetector window and will then hit the photodetector chip. The presence of two optical interfaces, of which at least one is redundant, also causes parasitic reflections and resonances and increase set-up cost.

Known in the art, there is U.S. Pat. No. 5,025,448 granted to SUDO. In this patent, SUDO describes a method and a gas cell for stabilizing frequency of semiconductor laser. The proposed cell has a reduced number of components by directly attaching lenses, bare fibers and photodetectors at the extremities of a cell (generally made of glass) in order to hermetically seal it. Although this method solves some of the drawbacks previously mentioned, this invention still presents several disadvantages. First, the input of the gas cell is not adapted for directly attaching an optical fiber to the cell and providing a collimated beam into the gas, which would be required if the light is to travel relatively long distances for detecting weak absorption lines of gases. In the proposed embodiment, the non collimated fiber is installed in a sealed tube passing through one end of the cell. The addition of the tube increases the number of orifices in the cell, the number of components, and also increases the risks of leaks.

Second, the output of the proposed cell is either a photodetector or a fiber obtained from a drawing rod of glass into a fiber. This last device does not offer the same flexibility and availability as a standard collimator made from a lens and an attached fiber. No solution is provided to provide a free-space collimated output beam.

Third, these cells do not allow to be used as modular units. They cannot be attached together to form multiple cavity cells or cannot be attached to a optoelectronic package.

Finally, this invention does not disclose how the optical components can be attached without using organic adhesives, nor how the gas cell, one filled, can be sealed without using the same organic materials or high temperature processes.

Also known in the art, is U.S. Pat. No. 4,119,363, which describes an hermetic metallic package that features an hermetic lens and fiber outputs. This invention provide very good hermeticity, and is intended to be filled with non-corrosive gas such as nitrogen. The invention, however, is constituted of many mechanical parts and seals that are not suited for very low cost gas cell fabrication.

U.S. Pat. Nos. 5,268,922 and 5,500,768 describe how laser sources or photodetectors can be packaged into an hermetic package having an optical output consisting of a window or a lens. These devices are not gas cells and have a large number of components, but illustrate the principle of using the lenses as components to seal the end of an hermetic cavity. U.S. Pat. No. 5,793,916 and U.S. patent application No. 2002/0118463 are other examples of specialized fibered devices that require hermetic seals but are still not dedicated to gas absorption measurements.

Therefore, there is a need for a new metallic gas cell that would overcome the drawbacks of the existing cells described above.

It would be advantageous to provide a method for manufacturing a metallic gas cell that possesses the minimum number of parts and has a low material cost.

It would be advantageous to provide a metallic gas cell that includes the minimum number of walls, a minimum number of joints and a minimum total length of hermetic joints in order to minimize the probability of a leak.

It would furthermore be advantageous to provide a metallic gas cell that does not possess end walls; the end optical components acting themselves as effective walls.

It would also be advantageous to provide a metallic gas cell wherein a limited number of components can be assembled in order to produce various cell configurations. This would reduce cost for stocking in high volume production while providing high product flexibility.

It would also be advantageous to provide a metallic gas cell having a reduced number of components by installing an optical fiber collimator or a collimating lens directly at the input of the gas cell, effectively sealing it.

It would also be advantageous to provide a metallic gas cell having a reduced number of components by installing a photodetector, a collimating lens or an optical fiber collimator directly at the output of the gas cell, effectively sealing it. This would eliminates the need for an output window, and would reduce the risk of parasitic resonances.

It would also be advantageous to provide a cell that can be sealed without using high temperatures.

It would also be advantageous to provide a metallic gas cell whose sealing process can be easily automated.

It would also be advantageous to provide a modular metallic gas cell which is attachable to another gas cell in order to provide multiple cavities gas cells while minimizing the number of optical components, therefore reducing the optical losses, parasitic reflections, resonances, and cost to a minimum.

It would also be advantageous to provide a metallic gas cell able to be attached to other types of optical modules, such as, for example, butterfly packages.

SUMMARY OF THE INVENTION

It is an object of the present invention to provide a metallic gas cell that satisfies the above-mentioned needs.

Accordingly, there is provided a metallic gas cell including a metallic casing having an input open end and an output open end, and an opening located therebetween. The metallic gas cell also includes an input and an output optical modules, each being respectively hermetically attached to one of the corresponding open ends. The metallic gas cell includes sealing means for sealing each of the optical modules in one of the corresponding open ends, thereby defining an airtight cavity in the casing when the opening is sealed. The metallic gas cell also includes an optical energy absorbing gas being enclosed within the cavity.

In a preferred embodiment of the present invention, the metallic gas cell is further provided with a sealable metallic filling tube tightly connected to the opening of the casing. The sealable metallic filling tube is advantageously sealed by a pinch-off thereof.

In another preferred embodiment of the present invention, each of the optical modules protrudes outwards of the casing, thereby rendering modular the metallic gas cell.

It is another object of the present invention to provide a method for manufacturing such a metallic gas cell.

Accordingly, there is provided, a method for manufacturing a metallic gas cell comprising the steps of:

a) providing a metallic casing having an input open end and an output open end, and a opening located therebetween;

b) disposing each of an input and an output optical modules inside the casing proximate the corresponding open end thereof;

c) heating at a predetermined temperature T1 the ends of the casing for sealing the optical modules to the casing, thereby defining a cavity in the casing;

d) creating a substantial vacuum inside the cavity;

e) filling the cavity with an optical energy absorbent gas with the opening; and;

f) sealing the opening.

Other features and advantages of the present invention will be better understood upon reading of preferred embodiments thereof with reference to the enclosed drawings.

BRIEF DESCRIPTION OF THE DRAWINGS

These and other objects and advantages of the invention will become apparent upon reading the detailed description and upon referring to the drawings in which:

FIG. 4 is a front sectional view of a metallic gas cell including an optical element according to another preferred embodiment of the present invention.

FIG. 5 is a front and side elevation view of two metallic gas cells which are connected together according to another preferred embodiment of the present invention.

FIG. 6 is a front sectional view of the two metallic gas cells shown in FIG. 5.

Figure 1:
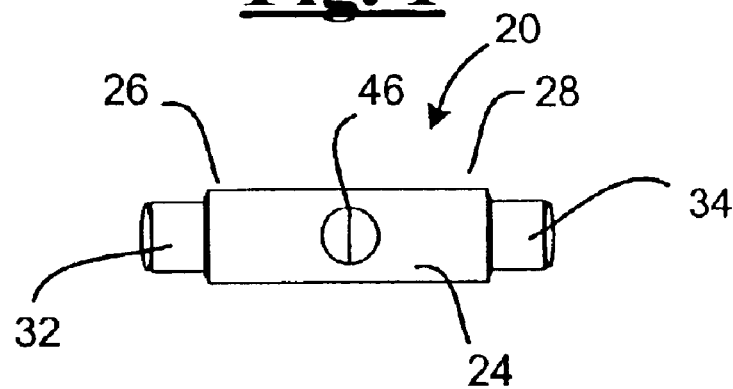
FIG. 1 is a top view of a metallic gas cell according to a preferred embodiment of the present invention.

While the invention will be described in conjunction with an example embodiment, it will be understood that it is not intended to limit the scope of the invention to such embodiment. On the contrary, it is intended to cover all alternatives, modifications and equivalents as may be included as defined by the appended claims.

DESCRIPTION OF PREFERRED EMBODIMENTS OF THE INVENTION

In the following description, similar features in the drawings have been given similar reference numerals and in order to weight down the figures, some elements are not referred to in some figures if they were already identified in a precedent figure.

The present invention concerns a metallic gas cell having a reduced number of parts, and a method for manufacturing the same. The main application of such a gas cell is the absolute calibration of an optical instrument generating or measuring a light signal, the light signal being provided by a laser source for example. Thus, the proposed invention can be used to create an optical frequency source which is stabilized on the absorption line of a gas. Of course, such a metallic gas cell can also be useful in other applications, and such applications are believed to be within the scope of the present invention.

Figure 2:
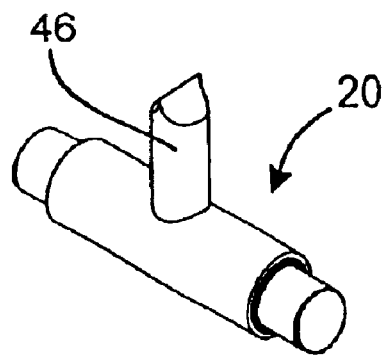
FIG. 2 is a front and side elevation view of the metallic gas cell shown in FIG. 1.
Figure 3:
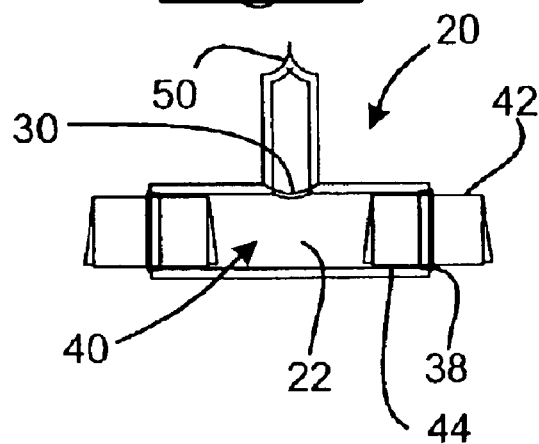
FIG. 3 is a front sectional view of the metallic gas cell shown in FIG. 1.
Figure 7:
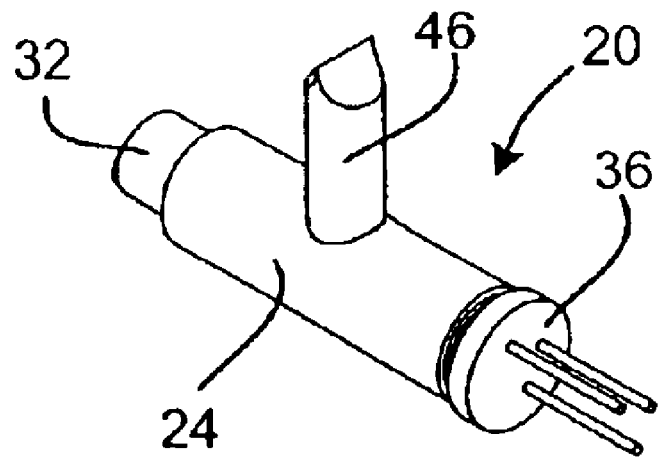
FIG. 7 is a front and side elevation view of another metallic gas cell according to another preferred embodiment of the present invention.
Figure 8:
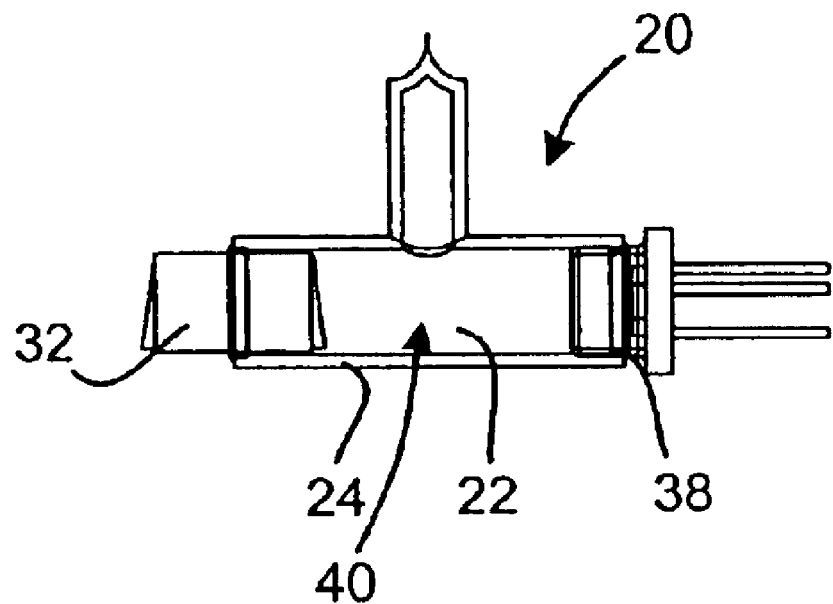
FIG. 8 is a front sectional view of the metallic gas cell shown in FIG. 7.
Figure 15:
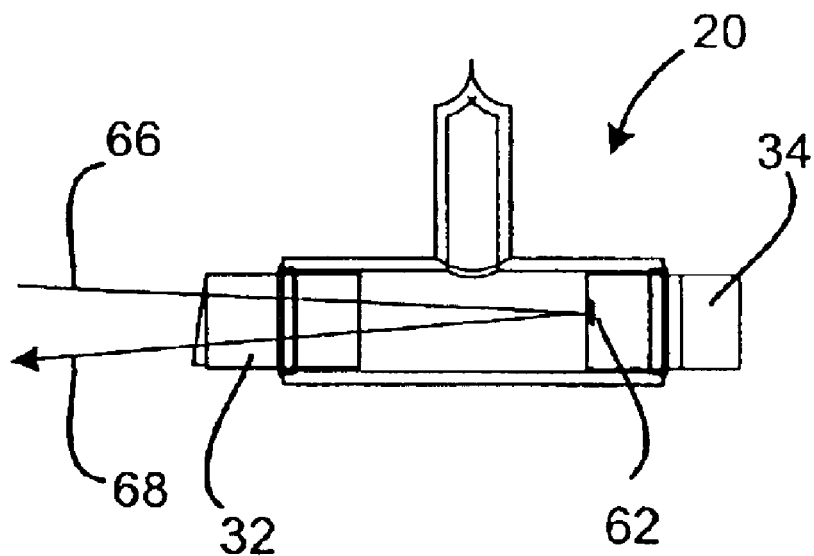
FIG. 15 is a front sectional view of a multipass metallic gas cell according to another preferred embodiment of the present invention.
Figure 16:
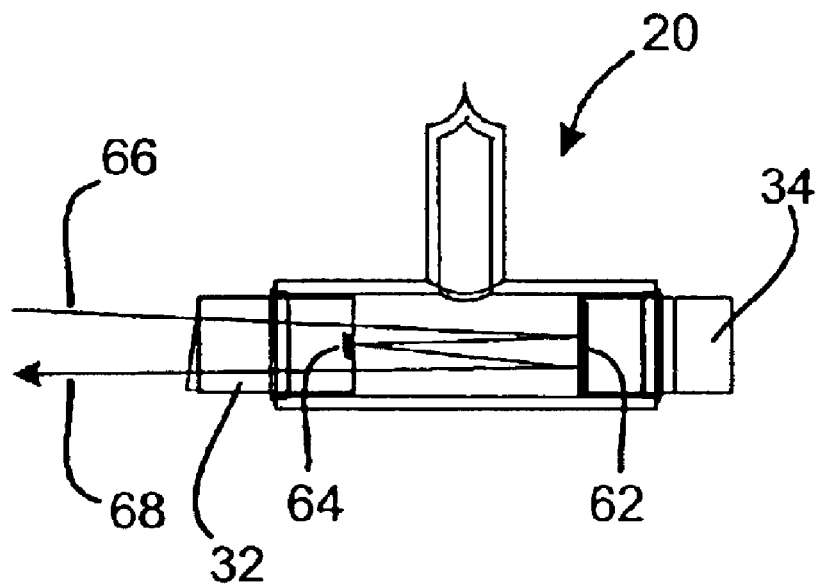
FIG. 16 is a front sectional view of another multipass metallic gas cell according to another preferred embodiment of the present invention.

Referring to FIGS. 1 to 3, there is shown a metallic gas cell 20 containing a gas 22 that is free inside the package. The metallic gas cell 20 includes a metallic casing 24 having an input open end 26 and an output open end 28, and a opening 30 located therebetween. The casing 24 may be made from any metallic material, advantageously presenting good sealing properties, but is preferably made of stainless steel or kovar. The illustrated casing 24 has a cylindrical shape but it should be understood that any other convenient shape of the casing 24 could naturally be used. The casing 24 may, for example, be obtained from a tube section or can also be obtained from a solid metallic part wherein a longitudinal cavity and an opening have been drilled. The metallic gas cell 20 also includes an input and an output optical modules 32, 34. Each of the optical modules 32, 34 is respectively hermetically attached to one of the corresponding open ends 26, 28. If the incoming light beam is not collimated, the input optical module 26 may be designed for collimating the light beam, thereby allowing a collimated propagation through the absorbing gas 22. The input optical module 32 may include a lens to collimate a free-space light beam. An optical fiber can be advantageously attached to the lens for providing a fibered input module that launch a collimated beam into the cell. Alternatively, the input optical module may also be a window for propagating an incoming light beam, which is already advantageously collimated, inside the cell 20 through the absorbing gas 22. The use of such a window allows the propagation of a light beam without acting thereon. The input optical module 32 may also be a laser or any other conventional optical elements or even a combination of several optical elements which are mounted together. The output optical module 34 may include a lens which may also be advantageously provided with an optical fiber. The output optical module 34 may also include a window or even a photodetector. As illustrated in FIGS. 7 and 8, a lidless can-type photodetector 36 could be used, the gas 22 should then be chosen for allowing a long life of the photodetector 36, that is the gas 22 should not degrade the parts and the wiring of the photodetector 36. The lenses, windows or other optical surfaces used in the input or output optical modules 32, 34 may be provided with opposed face which are not parallel without disturbing the assembling of the present cell. This might be necessary to prevent parasitic resonances between the optical components of the cell. Any kind of lens may be used according to a particular application, but the lens may advantageously be a rod lens, and more advantageously a graded index (GRIN) lens having a refractive index which varies along the radius of the lens. The metallic gas cell 20 also includes a sealing means 38 for sealing each of the optical modules 32, 34 in one of the corresponding open ends 26, 28 of the casing 24, thereby defining an airtight cavity 40 in the casing 24 when the opening 30 is sealed. The sealing means 38 is selected from group consisting of gluing, welding, brazing and soldering. In a preferred embodiment, each of input and output optical modules 32, 34 is advantageously provided with a metallized sidewall 42 for allowing an appropriate sealing of the modules 32, 34 in the casing 24. In this preferred embodiment, welding, brazing or soldering are used for sealing. In another preferred embodiment wherein the optical modules 32, 34 are not provided with a metallized sidewall, the sealing means 38 may advantageously be glass frit. Advantageously, each of the optical modules 32, 34 is hermetically attached to the internal wall 44 of the casing 24. Nevertheless, they can also be sealed at the extremities of the casing 24 only. The metallic gas cell 20 also include an optical energy absorbing gas 22 being enclosed within the cavity 40. Advantageously, the absorbing gas 22 enclosed within the cavity 40 is under a reduced pressure of no more than 1 atmosphere for providing narrower absorption linewidth. In order to measure weaker absorption lines, a multipass set-up could naturally be envisaged. FIGS. 15 and 16 illustrates such a multipass cell. In FIG. 15, an input beam is passed through the input module 32 and is propagated through the gas to the output module 34 which contain a reflective surface 62. This surface reflects light back to the input module where it exits the cell as a light beam 68. The input module could be a fibered collimator in which case the incoming and returning beam would be counter propagating in the same fiber. FIG. 16 illustrates a similar multipass module where the light beam passes more than two times in the gas cell. Such a cell has a similar construction as the previously described cell, except that part of the input module 32 is also covered with reflective surfaces 64. The collinear arrangement of the input and output modules in a preferably tubular cell ensures that the alignment of the reflective surface is accurately maintained. This allow the construction of cells with a high number of passes. By carefully choosing the mirror position and angles (not illustrated), the multipass cell can be made such that the light exists at the output module 34 instead of being reflected back to the input module 32.

Figure 23:
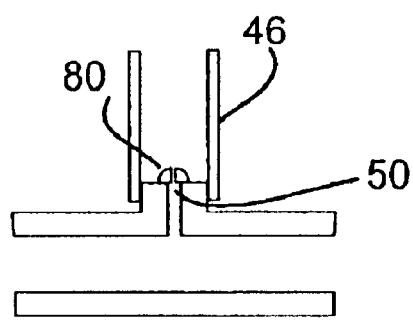
FIG. 23 illustrates a method to seal a metallic gas cell using a removable filling tube.

Still referring to FIGS. 1 to 3, the metallic gas cell 20 may be further provided with a sealable metallic filling tube 46 tightly connected to the opening 30 of the casing 24 for facilitating a filling of the gas cell 20. The sealable metallic filling tube 46 may be sealed by heating as conventional methods described above. However, in a preferred embodiment, the sealable metallic filling tube 46 is sealed by a pinch-off 50 thereof, as can be better seen in FIG. 3. The filling tube 46 may be made of any metallic material such as stainless steel for example, but a soft metal will advantageously facilitate the pinching of the filling tube 46. Such a pinch off can be done while a vacuum set-up is still connected to the cell and is maintaining the required gas pressure until the sealing is performed. The pinch off is made at room temperature and does not involve high temperatures. Simple pliers can be used to pinch the tube off. Another advantage of the present metallic gas cell 20 is that the pinching-off of the metal tube offers a known geometry which is substantially still the same, as opposed to the melting of the glass used in conventional gas cell. In another preferred embodiment which is not illustrated, one can use a temporary filling tube for filling the gas cell 20, sealing the opening 30, and then removing the temporary filling tube. This is illustrated in FIG. 23. A removable filling tube 46 could be temporarily attached around the small filling orifice 50 which is partly covered by solder 80. When the cell is evacuated and filled with gas, the base of the tube can be heated enough so that the solder 80 melts and completely obstructs the orifice. Once the solder is cooled, the filling tube can be removed. Low temperature solders could be used in order to avoid reactions with the gas. The unmelted solder preform could preferably be maintained in place within a countersink (not illustrated) to ensure it does not move during the cell evacuation and sealing processes.

Referring now to FIG. 4, the metallic gas cell 20 may further include an optical element 48 located inside the casing 24. Such optical element 48 may, for example, be a laser which emits light in two opposed directions towards the optical modules 32, 34. Element 48 may preferably be a Fabry-Perot resonator which would allow the optical beam traversing the cell to see a broadband periodic frequency response superposed with the absorption lines of the gas inside the cell.

In the preferred embodiment illustrated through FIGS. 1 to 6, each of the optical modules 32, 34 protrudes outwards of the casing 24. This renders modular the metallic gas cell 20 by allowing for means to connect them together in series. Referring particularly to FIGS. 5 and 6, there is shown two metallic gas cells 20 which are connected together. Thus, the two cells 20 share a common optical module 52. Such embodiment is very useful when a great alignment stability of the optical modules 32, 34 and 52 is required. The sharing of the common optical modules prevents using two separate components for sealing each cell, thus minimizing the optical losses or the probability of parasitic resonances. Such a gas cell allow different, incompatible gases to be interrogated by a single light beam since each cavity can be filled individually. An arbitrary number of cells can be placed in series, including multipass cells.

In another preferred embodiment which is not illustrated, the optical modules 32, 34 extend integrally inside the casing 24 and do not protrudes outwards in order to save space.

Figure 17:
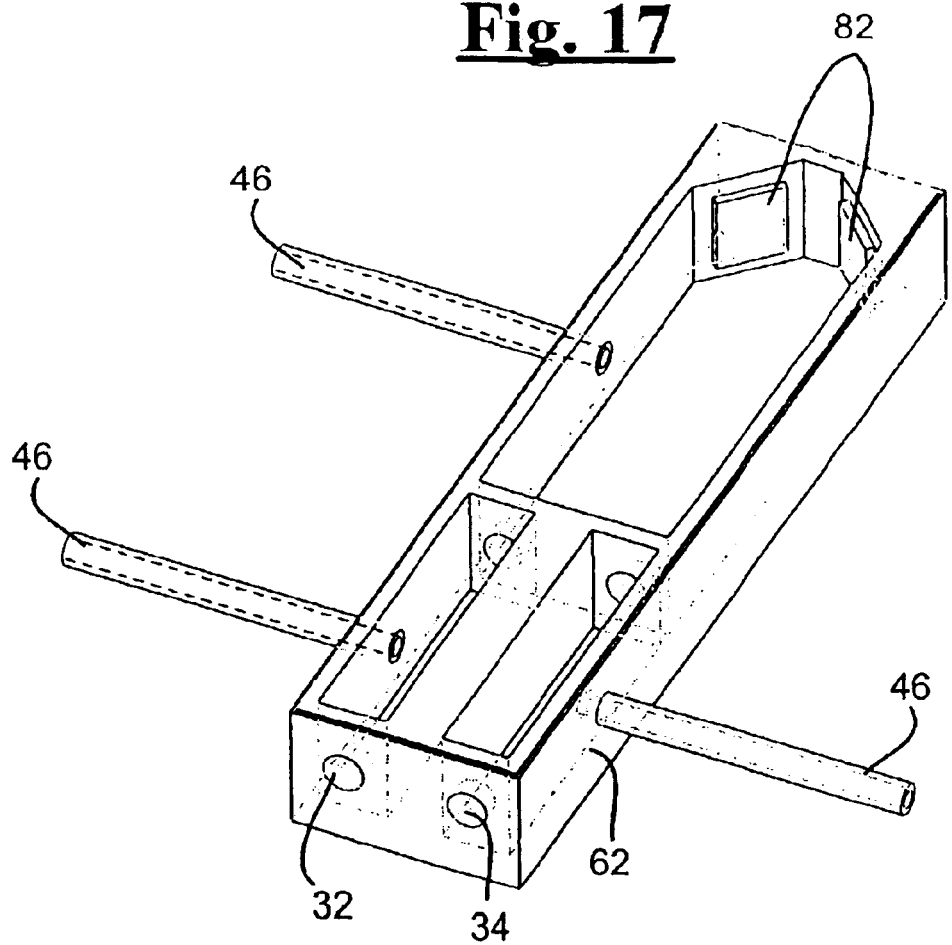
FIG. 17 is a front and side view of an integrated multicavity metallic gas cell according to another preferred embodiment of the present invention.

FIG. 17 illustrate another example of multicavity gas cell using a minimum number of components. In this setup, the input and output optical modules are placed on the same side of the cell, which is built by machining a metal block and drilling holes into it. If optical components have to be installed into the cell, as is the case with the illustrated cell having the two mirrors 82 placed in the large chamber, then there may be the required additional step of installing an hermetic lid (not illustrated) on each open section to provide an hermetic cavity. Each cavity is equipped with a filling orifice and preferably filling tubes 46. The illustrated multicavity cell uses lenses, windows or other optical components to provide hermeticity between the chambers and the exterior. These can be installed by any sealing method previously described. A preferable method is to solder metallized optical components directly on the metal casing. The illustrated cell provides means to pass the light beam twice into the gas filling the large chamber and shifts the light beam to allow it to pass through the two other smaller chambers. This configuration advantageously minimises the number of components and is very space efficient. Any number of chambers can be built into the same compact block, some of them which may contain optical components such as lasers, Fabry-Perot resonators, photodetectors etc, in an inert gas. Such a configuration would allow the one or more gas cell to be an intrinsic part of an optical component. Preferably, the described multicavity gas cell can be fabricated within a standard butterfly package format.

Figure 18:
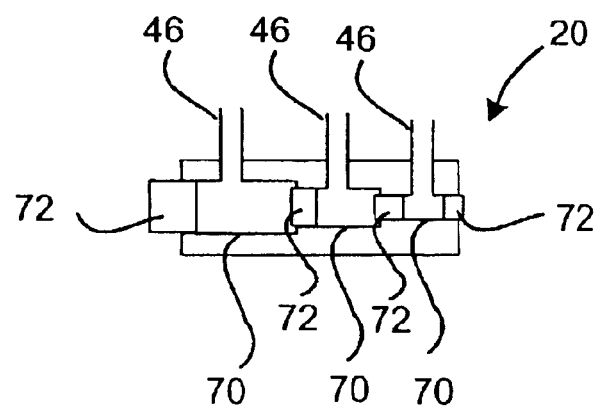
FIG. 18 is a front and side view of another integrated multicavity metallic gas cell according to another preferred embodiment of the present invention.

FIG. 18 illustrates another example of multicavity gas cell. This cell is constituted by boring a cylindrical hole 70 through a metal block, with preferably various diameters, and then drilling and installing filling tubes 46 that connect to each section of the cell. Lenses, windows or other optical components 72 are then placed at different positions in the tube and are hermetically attached in place. The various diameters of the different sections help the optical components to be held in place at specific positions in the tube. The optical components are preferably metallized and equipped with a solder preform so that all of the optical components may be soldered at one time by heating the cell as a whole. This set-up is compact, easy to manufacture, and allow multicavity gas cells to be fabricated using the minimum number of operations and components.

Referring to FIGS. 7 and 8, the output optical module is a photodetector 36. Preferably, a photodetector hermetically packaged in a metallic casing is used. The photodetector 36 is fixed by soldering, welding or brazing its casing to the cell body 24, therefore avoiding the need of using additional windows to hermetically seal the cell. Small inexpensive can-type photodetectors could be used for that purpose. The input module 32 ensures that the incoming light is passed through the gas and is accurately directed towards the active region of the detector. Any king of input modules described previously could be used. Once the cavity 40 is filled with absorbing gas 22, the photodetector 36 will detect the light beam reaching it after it has been absorbed by the gas 22 at some specific frequencies. The gas cell 20 can therefore be used to lock a laser on a reference absorption line or to calibrate the frequency of a tunable laser.

Figure 9:
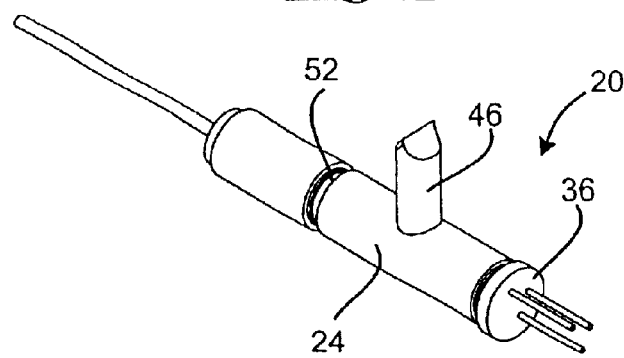
FIG. 9 is a front and side elevation view of a metallic gas cell connected to a photodetector according to another preferred embodiment of the present invention.
Figure 10:
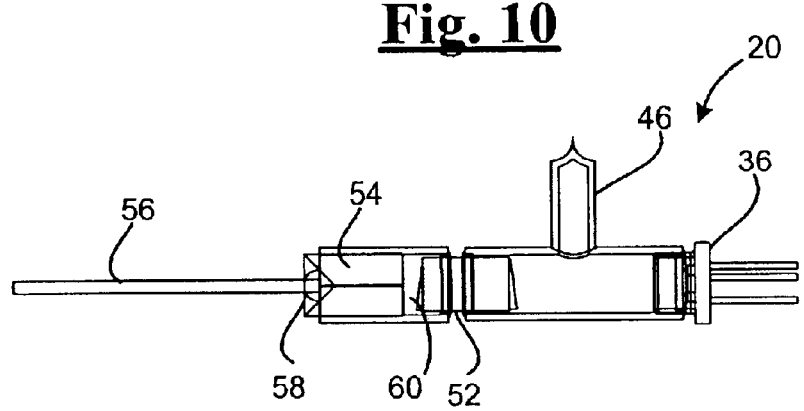
FIG. 10 is a front sectional view of the metallic gas cells shown in FIG. 9.
Figure 11:
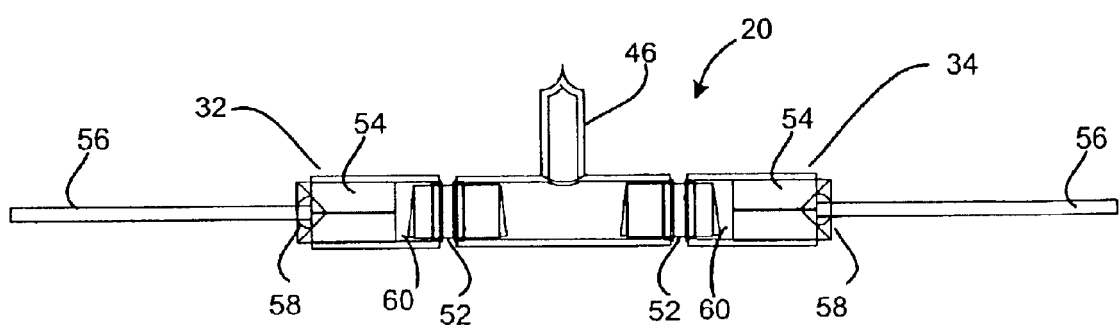
FIG. 11 is a front sectional view of a metallic gas cell connected to two fiber collimators according to another preferred embodiment of the present invention.

Referring to FIGS. 9 to 11, there is shown different arrangements of a gas cell 20 connected to other optical devices and sharing a common optical element 52, which is preferably a collimator lens. Of course, any number of such gas cell 20 can be connected together. In the arrangement shown in FIGS. 9 and 10, the output optical module 34 is a photodetector 36 and the input optical module 32 include a ferrule 54, preferably made of ceramics, for maintaining an optical fiber 56. The optical fiber 56 is preferably attached to the ferrule 54 with epoxy 58. An optional epoxy portion 60 having an appropriate refractive index may advantageously be inserted between the ferrule 54 and the common optical element 32. FIG. 11 illustrates an arrangement including a metallic gas cells 20 wherein each of the external optical modules 32, 34 is provided with an optical fiber 56. This provides an easy integration of such gas cell in existing optical systems such as Optical Spectrum Analysers.

Figure 12:
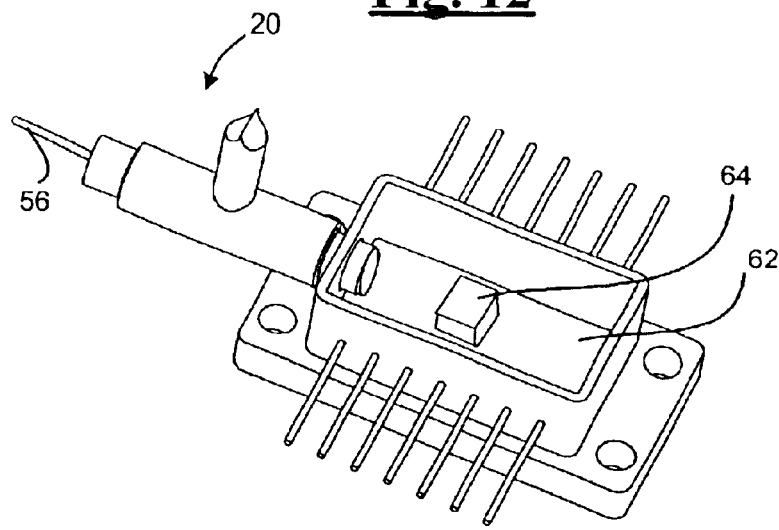
FIG. 12 is a front and side elevation view of a metallic gas cell which is connected to an optical package according to another preferred embodiment of the present invention.
Figure 13:
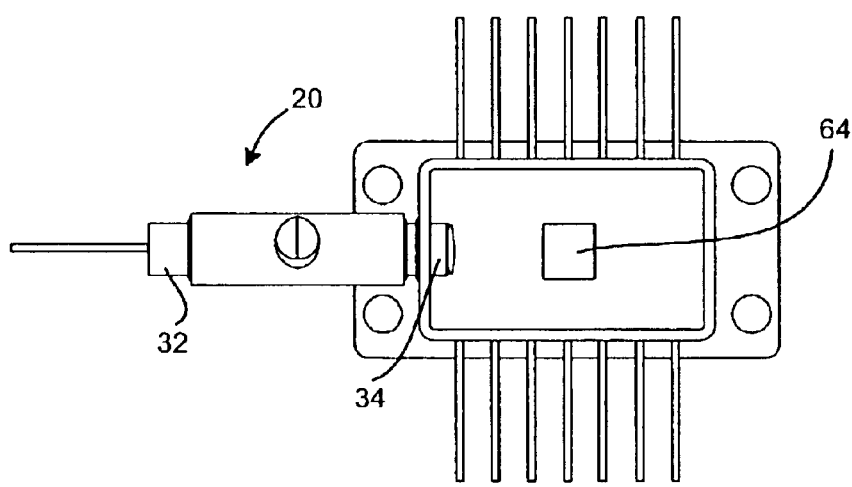
FIG. 13 is a top view of the arrangement shown in FIG. 12.
Figure 14:
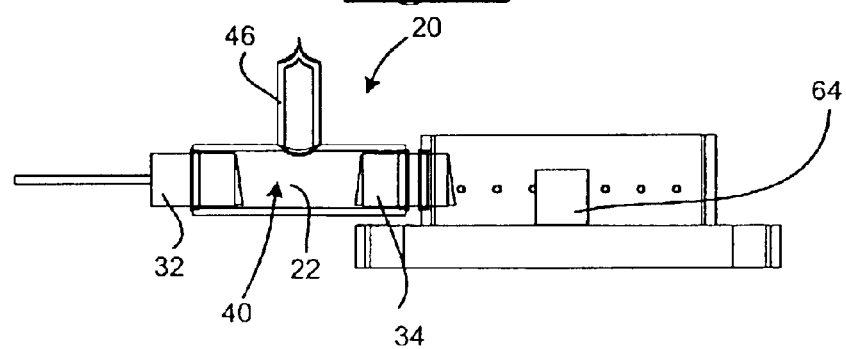
FIG. 14 is a side view of the arrangement shown in FIG. 12.
Figure 22:
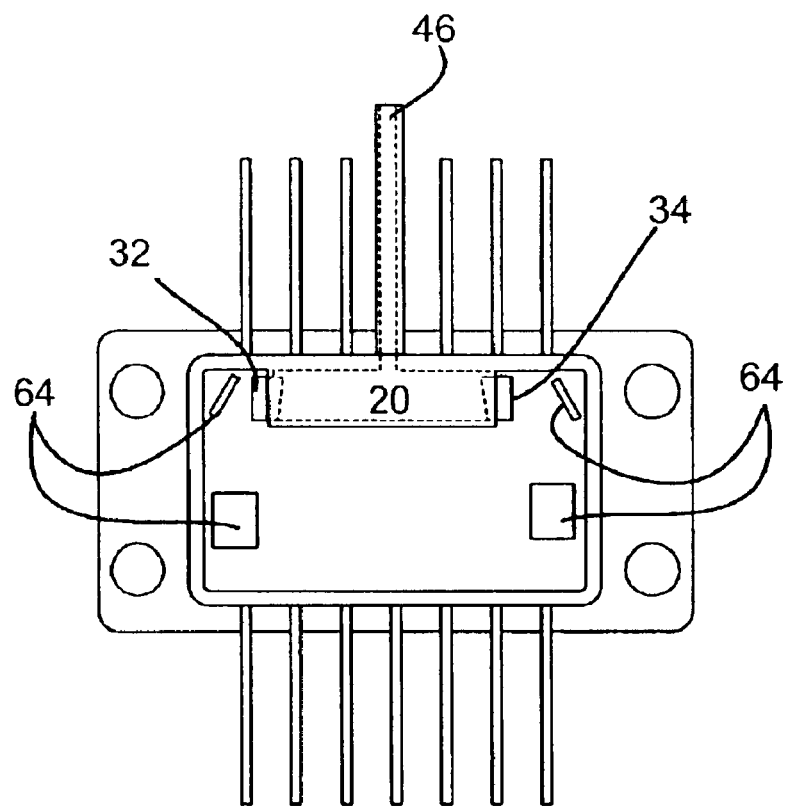
FIG. 22 illustrates a top view of a Butterfly package integrating a metallic gas cell.

Referring now to FIGS. 12 to 14, such a gas cell 20 may be connected to a conventional package 62 having optical components 64 mounted therein. For example, a white light source or even a laser source may be mounted inside the package 62 for sending light inside the gas cell 20 for propagating through the absorbing gas 22. This gas cell allows the package itself to be assembled using conventional techniques while having access to a high hermeticity gas cell. Various methods could be used to fabricate such a gas cell directly within the optical package, as illustrated in FIG. 22. In this embodiment, the hermetic gas cell 20 is fabricated directly into the Butterfly-type package. The filling tube 46 is placed on the outside of the package to allow the cell to be evacuated and filled with the desired gas. Optical modules, preferably metallized windows, are soldered at the extremities of the cell. The optical components 64 within the Butterfly package sent part of their light into the cell to use the gas as an optical frequency reference.

It should be noted that in the previous embodiments, various materials could be used for constructing the lens or optical windows. Conventional materials may be compatible with a number of gases. If highly reactive gases such as HF is used, the lens or windows should preferably be made of sapphire which does not react to that gas.

It is also to be noted that conventional half-pitch or full-pitch GRIM lenses could advantageously be used as effective optical windows since they do not modify the direction or divergence of an optical beam. These type of lenses may be easier to find with a metallization than other types of windows since they are commonly used (with other pitch) in the fabrication of fiber collimators.

The preferred shape for the gas cell or the optical components is cylindrical, since these minimize the amount of material, are easier to machine, and provide the shortest seal lengths. Other shapes could be used, however.

Figure 19:
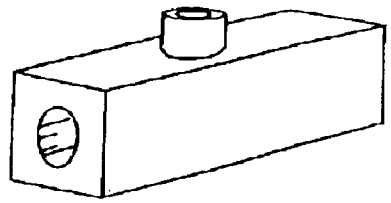
FIG. 19 is a front and side view of a metallic gas cell built from machining a metal block according to another preferred embodiment of the present invention.
Figure 20:
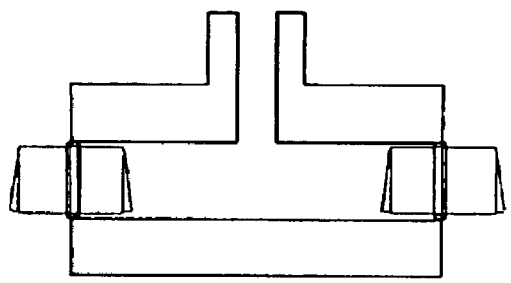
FIG. 20 is a front sectional view of the arrangement shown in FIG. 19.

FIGS. 19 and 20 illustrate a gas cell which has its cavity and filling tube machined from a single metal block. The cavity and filling tube are formed by two drilling operations. The tube exterior can be further machined to allow easier connection to a vacuum system. The exterior of the cell do not have to be cylindrical, and can be made square or rectangle to allow easier installation within a package or other optical setup. Fixation holes (not illustrated) can be machined in the cell to allow it to be secured to a surface with screws. Other inexpensive methods for fabricating such a gas cell consists in using metal casing based on magnesium powder or other materials.

Figure 21:
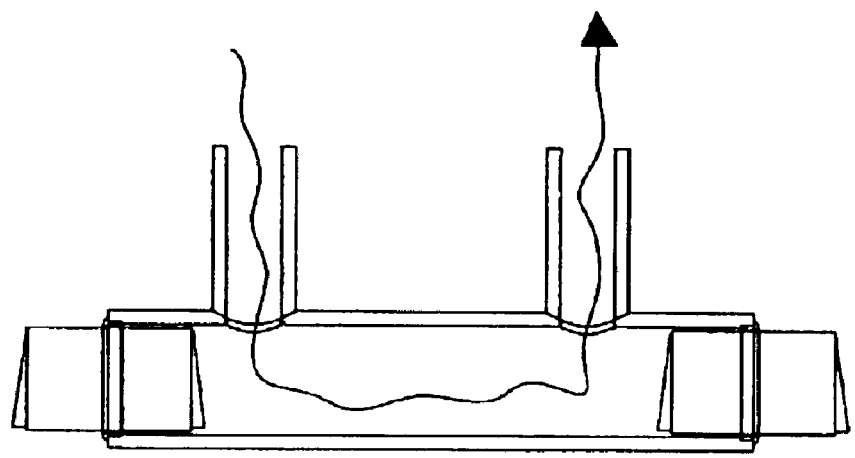
FIG. 21 is a front sectional view of a metallic gas cell used to optically interrogate a flowing gas according to another preferred embodiment of the present invention.

FIG. 21 illustrate a modified hermetic gas cell that possess an input and output tubes. The cell is fabricated using the same techniques as previously described. This cell however allow a gas to flow from one tube to the other, allowing the optical beam to interrogate the content of that gas. This cell configuration can be used to monitor gas composition in environmental or industrial applications.

It should be noted that in order to achieve a high quality gas cell, it may be necessary to heat the cell and pump it with a high performance vacuum pump in order to allow the molecules to degass from the interior surfaces of the cell. The higher the heating temperature is, the faster will be the degassing. Heating should not exceed the maximum temperature of the optical components and solder, in order to avoid damaging the cell. It may be advantageous to install the fibers only after the gas cell have been sealed with the lens, heated degassed and sealed. This would avoid damaging the fiber coating and the attachment epoxy.

A method for manufacturing the metallic gas cell is also provided. The method includes the steps of:
  a) providing a metallic casing having an input open end and an output open end, and a opening located therebetween;
  b) disposing each of an input and an output optical modules inside said casing proximate the corresponding open end thereof;
  c) heating at a predetermined temperature T1 said ends of said casing for sealing said optical modules to the casing, thereby defining a cavity in said casing;
  d) creating a substantial vacuum inside said cavity;
  e) filling said cavity with an optical energy absorbent gas with said opening; and;
  f) sealing said opening.

The method may advantageously further include the step of sealing a metallic filling tube to the opening at a predetermined temperature T2 higher than T1 prior to step b) for facilitating the filling of the gas cell. In this case, the step of sealing the opening preferably includes a pinching of the metallic filling tube but any other convenient means such as those described above may also be envisaged. Temperature T1 being lower than temperature T2, the heating of the open ends of the casing would not affect the sealing of the filling tube. Preferably, temperatures for T2 should be around 620–980° C. if Ag/Cu based solders are used. T1 preferably ranges between 150 and 280° C. by using InPbAg, SnPb or AuSn solders.

Vacuum can be created by pumping the air inside the cell through the opening or the filling tube. Once a sufficient vacuum is made, the absolute reference gas can be inserted inside the cavity and the opening or filling tube can be sealed. The cell can be filled in different way. In the case a filling tube is used, the tube is preferably sealed by pinching thereof once the gas is inside the cell and while the filling pump is still connected to the filling tube. If a single opening is used, the whole gas cell is put in a vacuum chamber and filled with gas, and then the opening can be sealed by soldering or any convenient means providing an airtight seal. Then, the gas cell can be returned to normal external atmosphere while maintaining its internal gas pressure. This specific construction allows for the filling of the gas cell without exposing the absorbing gas to high temperatures generally required for the sealing of the end walls.

The method for manufacturing the metallic gas cell according to the present invention may further include the step of metallizing a sidewall of each of the optical modules prior to step b). Moreover, The method for manufacturing the metallic gas cell advantageously includes the step of cleaning the inside of the casing prior to the heating of the ends of the casing. Furthermore, the method may also advantageously include the step of degassing at a predetermined temperature T3 lower than T1 the metallic gas cell after sufficient vacuum has been created. Once the opening is sealed, the method may advantageously include an additional step of attaching an optical fiber to each of the optical modules with an epoxy glue for providing a fibered gas cell that can be used in most existing system. With this particular construction, the epoxy will not be exposed to high temperatures that could alter the physical integrity of the epoxy. Temperature T3 is preferably in the range of 80–120° C.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention. For example, the illustrated metallic gas cells are provided with cylindrical element but any other geometric shape could also be envisaged and is believed to be within the scope of the present invention.

What is claimed is:
1. A method for manufacturing a metallic gas cell comprising the steps of:
  (a) providing a metallic casing having an input open end and an output open end, and a opening located therebetween;
  (b) sealing a metallic filling tube to said opening at a predetermined temperature T2 that is higher than a predetermined temperature T1;
  (c) disposing each of an input and an output optical modules inside said casing proximate the corresponding open end thereof;
  (d) heating at the predetermined temperature T1 said ends of said casing for sealing said optical modules to the casing, thereby defining a cavity in said casing;
  (e) creating a substantial vacuum inside said cavity;
  (f) filling said cavity with an optical energy absorbent gas with said opening; and
  (g) sealing said opening.

2. The method for manufacturing a metallic gas cell according to claim 1, wherein the step of sealing said opening comprises a pinching of said metallic filling tube.

3. The method for manufacturing a metallic gas cell according to claim 1 further comprising the step of metallizing a sidewall of each of said optical modules prior to step c).

4. The method for manufacturing a metallic gas cell according to claim 1 further comprising the step of cleaning inside of the casing prior to step d).

5. The method for manufacturing a metallic gas cell according to claim 1, wherein said step e) further comprises degassing at a predetermined temperature T3 lower than T1 said metallic gas cell.

6. The method for manufacturing a metallic gas cell according to claim 1, further comprising the step h) of attaching an optical fiber to each of said optical modules with an epoxy glue.

* * * * *